United States Patent
Farley et al.

(10) Patent No.: US 11,931,019 B2
(45) Date of Patent: Mar. 19, 2024

(54) SURGICAL RETRACTOR HAVING CLAMPING MECHANISM

(71) Applicant: Thompson Surgical Instruments, Inc., Traverse City, MI (US)

(72) Inventors: Dan Farley, Traverse City, MI (US); Josh Delickta, Elk Rapids, MI (US); Christopher T. Martin, Empire, MI (US); Travis Witulski, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 446 days.

(21) Appl. No.: 17/202,665

(22) Filed: Mar. 16, 2021

(65) Prior Publication Data

US 2021/0196255 A1    Jul. 1, 2021

Related U.S. Application Data

(63) Continuation of application No. 16/299,400, filed on Mar. 12, 2019, now Pat. No. 10,952,713, which is a continuation of application No. 15/232,466, filed on Aug. 9, 2016, now Pat. No. 10,226,241.

(60) Provisional application No. 62/203,144, filed on Aug. 10, 2015.

(51) Int. Cl.
*A61B 17/02* (2006.01)
*F16B 2/18* (2006.01)
*A61B 90/57* (2016.01)

(52) U.S. Cl.
CPC ............... *A61B 17/02* (2013.01); *F16B 2/18* (2013.01); *A61B 90/57* (2016.02)

(58) Field of Classification Search
CPC .................................. A61B 17/02; F16B 2/18
See application file for complete search history.

(56) References Cited

U.S. PATENT DOCUMENTS

| | | |
|---|---|---|
| 2,893,378 A | 7/1959 | Cooper |
| 3,221,743 A | 12/1965 | Thompson et al. |
| 3,965,890 A | 6/1976 | Gauthier |
| 4,421,108 A | 12/1983 | Cabrera et al. |
| 4,596,484 A | 6/1986 | Nakatani |
| 4,617,916 A | 10/1986 | LeVahn et al. |
| 4,813,401 A | 3/1989 | Grieshaber |
| 4,971,038 A | 11/1990 | Farley |
| 5,020,195 A | 6/1991 | LeVahn |
| 5,025,780 A | 6/1991 | Farley |
| 5,224,680 A | 7/1993 | Greenstein et al. |
| 5,515,744 A | 5/1996 | Liao |
| 5,609,565 A | 3/1997 | Nakamura |
| 5,846,192 A | 12/1998 | Teixido |
| 5,897,087 A | 4/1999 | Farley |
| 6,033,363 A | 3/2000 | Farley et al. |

(Continued)

*Primary Examiner* — Andrew Yang
(74) *Attorney, Agent, or Firm* — McAndrews, Held & Malloy, Ltd.

(57) ABSTRACT

A clamp for a surgical retractor system. The clamp has a tapered conically shaped washer against and through which clamping force is applied to place the clamp in a clamped position. The clamping force is applied by a cam head connected to a central shaft. A locking pin connects the cam head to the shaft. Apertures are provided in the clamp for receiving rod ends of a surgical retractor. Such apertures are circular and are positioned to be closer to the top and bottom edges of the clamp portion of the clamp than to the end edge of the clamp portion.

20 Claims, 9 Drawing Sheets

(56) References Cited

U.S. PATENT DOCUMENTS

| | | |
|---|---|---|
| 6,302,843 B1 | 10/2001 | Lees et al. |
| 6,474,900 B2 | 11/2002 | Feng |
| 6,511,423 B2 | 1/2003 | Farley |
| 7,125,380 B2 | 10/2006 | Yager |
| 7,297,107 B1 | 11/2007 | Bjork et al. |
| 7,320,666 B2 | 1/2008 | Bjork et al. |
| 7,553,279 B1 | 6/2009 | Phillips et al. |
| 7,556,229 B2 | 7/2009 | Elliott et al. |
| 7,562,855 B2 | 7/2009 | Oetlinger |
| 7,758,502 B2 | 7/2010 | Phillips et al. |
| 9,089,299 B2 | 7/2015 | Nowak et al. |
| 9,636,785 B2 | 5/2017 | Traver et al. |
| 2008/0247818 A1 | 10/2008 | Oesch et al. |

SURGICAL RETRACTOR HAVING CLAMPING MECHANISM

BACKGROUND OF THE INVENTION

The present invention relates to retractor systems for use during invasive surgical medical procedures.

During surgical medical procedures, a surgeon will typically make an incision in a patient to access the site of interest for the particular surgical procedure. To maintain clear access to the site of interest, a surgical retractor system is typically utilized. A surgical retractor system typically consists of a rail clamp, a frame connected to the rail clamp by a universal connecting joint mechanism, and retractor blades that are connected to the frame by additional universal connecting joint mechanisms. The rail clamp is commonly secured to an operating table and provides a fixed and sturdy support for the frame and the retractor blades. Each of the components in a typical surgical retractor system is conventionally made of stainless steel. The reason that stainless steel is generally used is that stainless steel is easily sterilized. As would be expected, before any use of the surgical retractor system can be made during a surgical procedure, the system must be thoroughly sterilized for the protection of the patient.

Surgical retractor systems have been made of other materials in the past, such as aluminum and titanium. The common characteristic of all of these materials is that they are highly durable and easily sterilized. That is, these materials are not porous and easily lend themselves to typical sterilization procedures used in modern day hospitals.

Accordingly, it is an object of the invention to provide a surgical retractor system that can be used confidently in surgical procedures.

It is a further object of the invention to provide a universal clamping mechanism for a surgical retractor system.

It is a further object of the invention to provide a clamping mechanism that is strong against wear caused by continual use of the clamping mechanism over time.

BRIEF SUMMARY OF THE INVENTION

These and other objects of the invention are achieved in a surgical retractor system which includes at least one clamp. The surgical retractor system may include a cam head having a flat latching surface, a tapered area washer configured to receive a central shaft and apply force to the at least one clamp, a locking pin configured to connect the central shaft to the cam head, and/or an offset applied to a passage used to clamp rods in the surgical retractor system.

DETAILED DESCRIPTION OF THE INVENTION

In the following detailed description, spatially orienting terms are used such as "left," "right," "vertical," "horizontal," and the like. It is to be understood that these terms are used for convenience of description of the preferred embodiments by reference to the drawings. These terms do not necessarily describe the absolute location in space, such as left, right, upward, downward, etc., that any part must assume.

Figure 1:
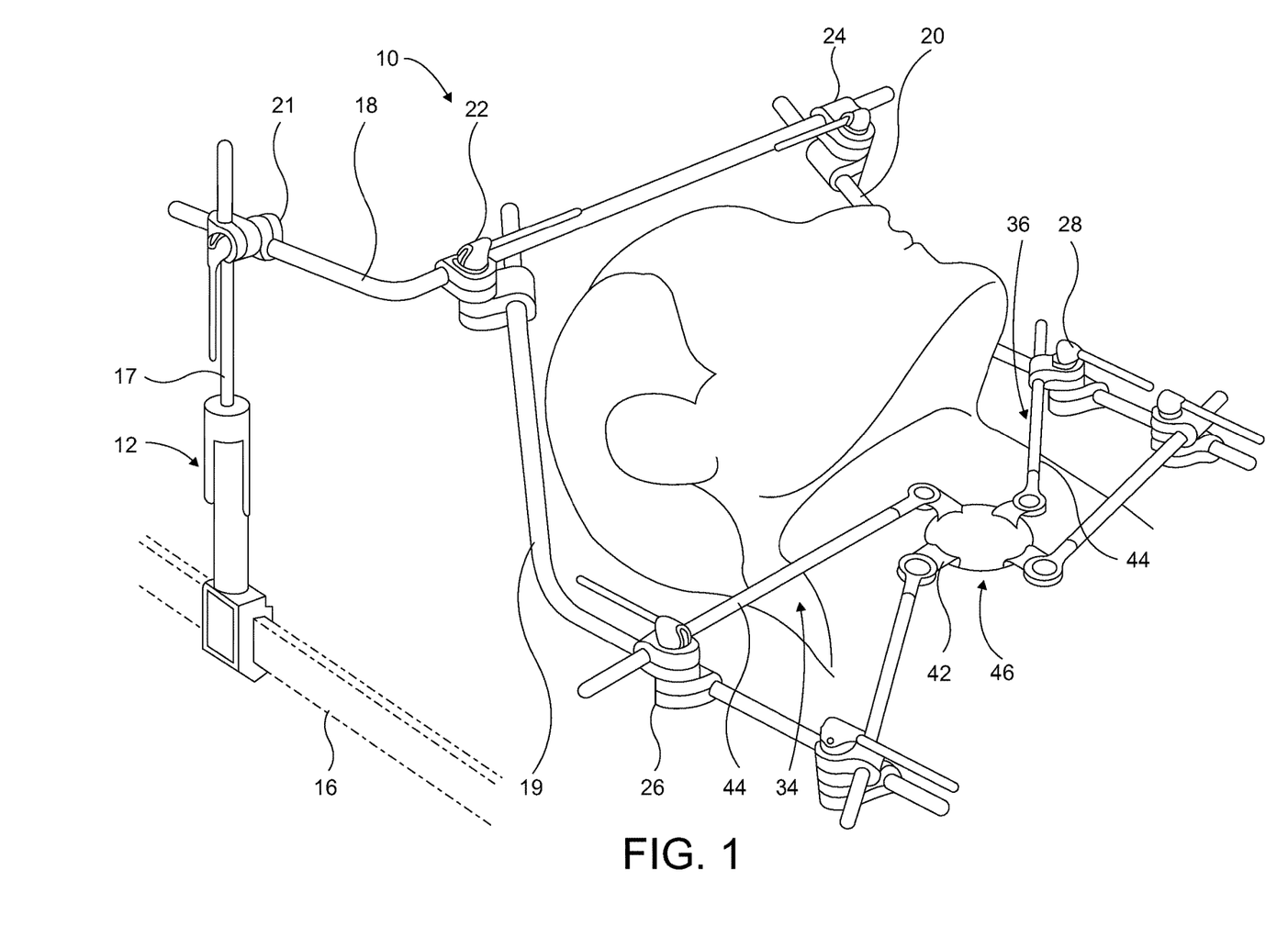
FIG. 1 is a perspective view of a typical surgical retractor system.

As shown in FIG. 1, a surgical retraction system 10 includes an adjustable rail clamp 12 which is securable to a conventional surgical table 16. A second adjustable rail clamp (not shown) may be secured to the opposite side of the surgical table for increased stability if desired or needed. A post 17 extends vertically from clamp 12 to provide support for a cross bar 18 which in turn provides support for a pair of extension arms 19, 20. Cross bar 18 is secured to post 17 by a multi-directional joint clamp 21. Extension arms 19, 20 are respectively secured to cross bar 18 by a pair of multi-directional joint clamps 22, 24. Additional joint clamps 26, 28 are disposed along extension arms 19, 20 for rigidly securing any number of retractor blades 34, 36 to extension arms 19, 20. As will suggest itself, extension arm 19 may be secured directly to post 17 by a joint clamp, thus in many circumstances eliminating the need for cross bar 18.

The purpose of this frame is to securely connect the retractor blades 34, 36 to the rail clamp 12 to eliminate unwanted relative movement between the retractor blades 34, 36 and the surgical table 16, this may be accomplished by connecting the retractor blades to the cross bar 18 directly or through extension arms 19, 20, or, as already noted, by connecting extension arms 19, 20 directly to the rail clamp.

Each retractor blade 34, 36 includes a blade portion 42 and a retractor arm 44. Blade portion 42 extends downwardly into the incision 46 made by the surgeon. Blade portion 42 is used to retract anatomy to make the incision 46 accessible to the surgeon.

Figure 2:
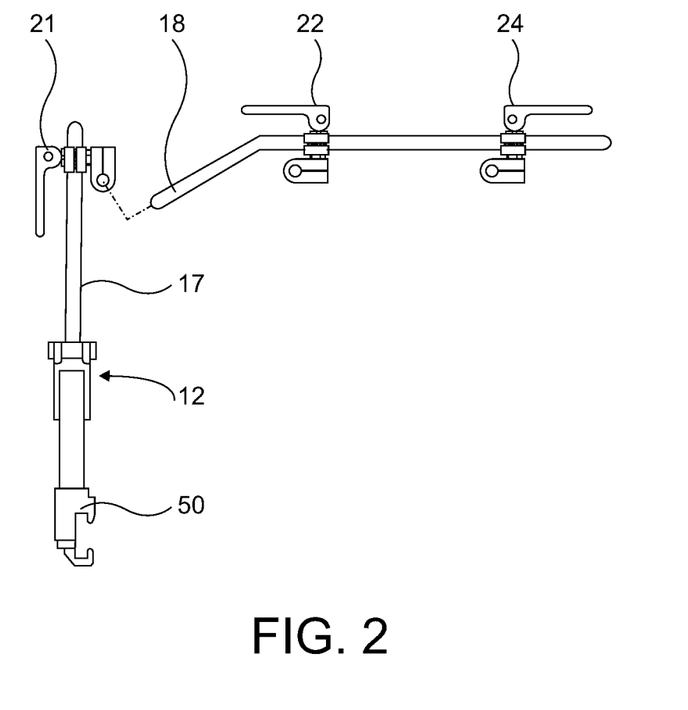
FIG. 2 is an elevated view of a rail clamp with a universal clamping mechanism of the present invention and a cross bar for insertion into the insulated universal clamping mechanism.
Figure 3:
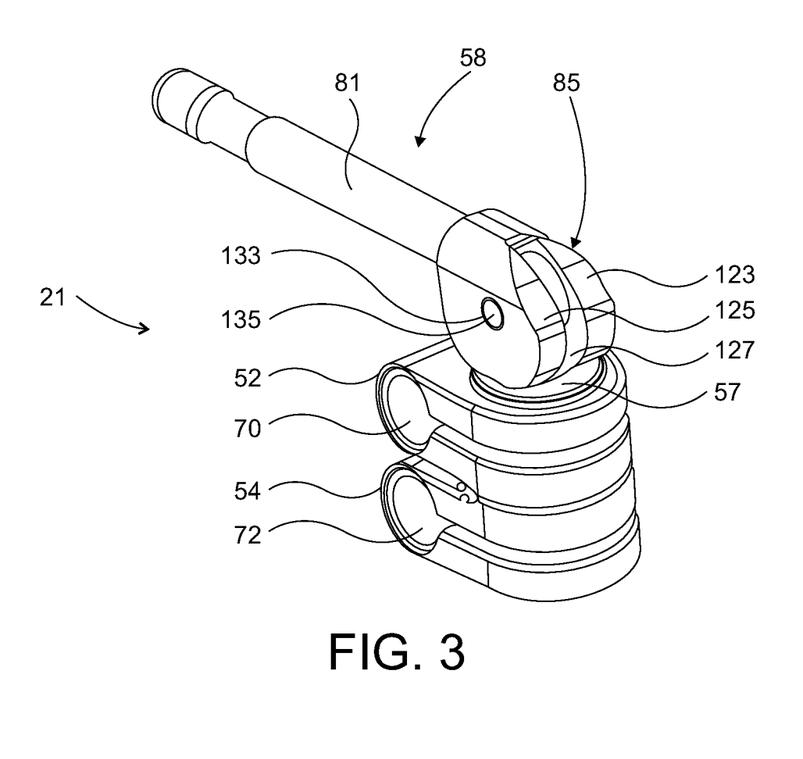
FIG. 3 is a perspective view of the universal clamping mechanism of the present invention with an insulating sleeve.

FIG. 2 is an elevated view of the rail clamp 12 and cross bar 18. Of course, as noted above, extension arm 19 or 20 may be connected directly to adjustable rail clamp 12. The rail clamp includes a clamp 50 that may be secured to surgical table 16 (FIG. 1). This may be a conventional clamp as presently used in the industry and provides for a secure attachment of the adjustable rail clamp 12 to the surgical table 16. Multi-directional joint clamp 21 is shown at the upper most extremity of post 17. This position of the multi-directional joint clamp 21 enables the user to locate cross bar 18 at a height sufficient for the surgical retractor system 10 (FIG. 1) to be used during surgical procedures. FIG. 2 further shows joint clamps 22, 24 in their position on cross bar 18. Clamps 22 and 24 may be identical to each other or different depending on the intended use of each of those clamps. Additionally, these joint clamps 22, 24 may each be the same as or different to the multi-directional joint clamp 21 on post 17.

Referring to FIGS. 3-5 and 14, multi-directional joint clamp 21 includes a first clamp 52 and a second clamp 54. Joint clamp 21 includes a central shaft 56 as well as a cam lever 58 for bringing first clamp 52 and second clamp 54 into a clamping position or into an unclamping position. Joint clamp 21 may also include a washer 57 positioned between the cam lever 58 and the first clamp 52.

The first clamp 52 may include a passage 70, which is intended to accommodate, for example, post 17 of rail clamp 12 (FIG. 2). Similarly, the second clamp 54 may include a passage 72. Passage 72 is intended to accommodate, for example, cross bar 18 (FIG. 2). This type of joint clamp is more fully described in U.S. Pat. Nos. 5,897,087 and 6,033,363, which are incorporated herein by reference.

The first cylindrical passage 70 of the first clamp 52 is defined by a broken cylindrical surface 71. The cylindrical surface 71 is broken along two parallel legs 73, 74 which run the axial length of the surface 71 to define a gap 75. Legs 73, 74 are movable with respect to one another in order to shorten the gap 75 and thus constrict the area circumscribed by cylindrical surface 71. Each leg 73, 74 defines a respective planar surface 76, 77. Each planar surface 76, 77 is generally parallel to the longitudinal axis of cylindrical passage 70. The application of a clamping forces directs forces against an upper surface 78*a* and a lower surface 78*b* of the first clamp 52 in a direction toward the gap 75 and parallel to the longitudinal axis of shaft 56 and serves to move planar surfaces 76, 77 toward each other constricting the area within cylindrical passage 70.

Similarly, the second cylindrical passage 72 of the second clamp 54 is defined by a broken cylindrical surface 80. The cylindrical surface 80 is broken along two parallel legs 82, 84 which run the axial length of the surface 80 to define a gap 86. Legs 82, 84 are movable with respect to one another in order to shorten the gap 86 and thus constrict the area circumscribed by cylindrical surface 80. Each legs 82, 84 defines a respective planar surface 90, 92. Each planar surface 90, 92 is generally parallel to the longitudinal axis of cylindrical passage 80. The application of a clamping force directs forces against an upper surface 94*a* and a lower surface 94*b* of the second clamp 54 in a direction toward the gap 86 and parallel to the longitudinal axis of shaft 56 and serves to move planar surfaces 90, 92 toward each other constricting the area within cylindrical passage 72.

The clamp 52, 54 further include locking teeth. In particular, a first set of locking teeth 99*b* is disposed on the lower surface 78*b* of first clamp 52 and a second set of locking teeth 99*a* is disposed on the upper surface 94*a* of second clamp member 54. The sets of locking teeth 99*a*, 99*b* engage each other when clamp members 52, 54 are compressed together by cam lever 58, thereby fixing the positions of clamps 52, 54 relative to one another.

The cam lever 58 includes a cylindrical shaped handle 81 having a distal end 83 connected to a cam head 85. Cam head 85 is pivotally mounted to central shaft 56 such that rotation of the cam lever 58 about a pivot axis 88 brings first clamp 52 and second clamp 54 into clamping positions and unclamping positions. The shaft 56 may be cylindrical in cross section and may extend through the cylindrical apertures 112, 116 in clamp members 52, 54.

Figure 4:
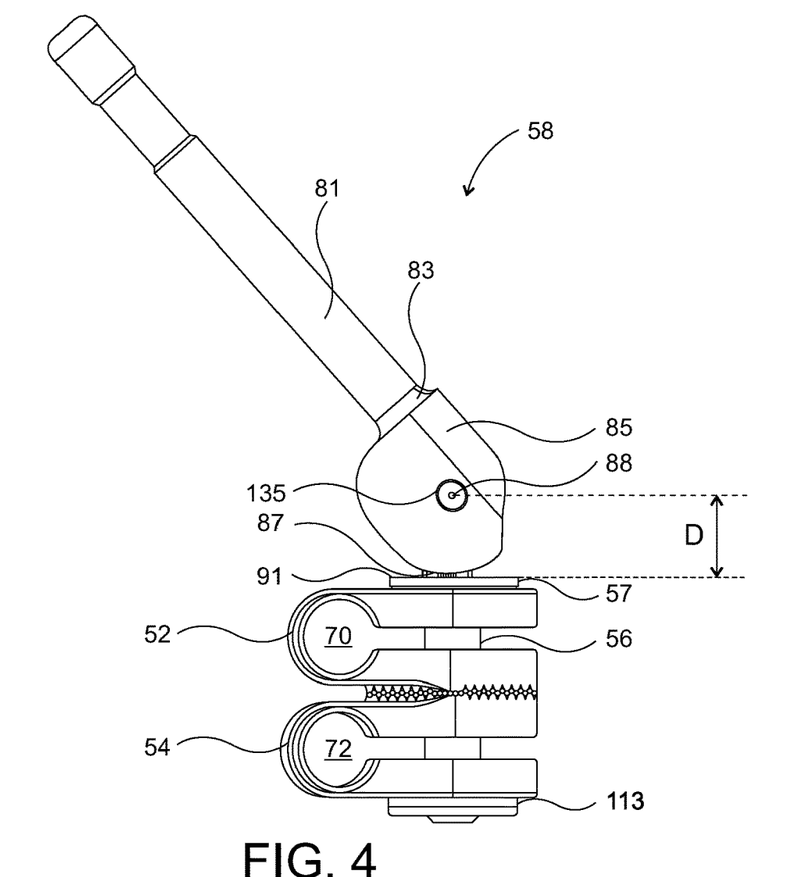
FIG. 4 is a side view of the universal clamping mechanism of FIG. 3 and in its open position.
Figure 5:
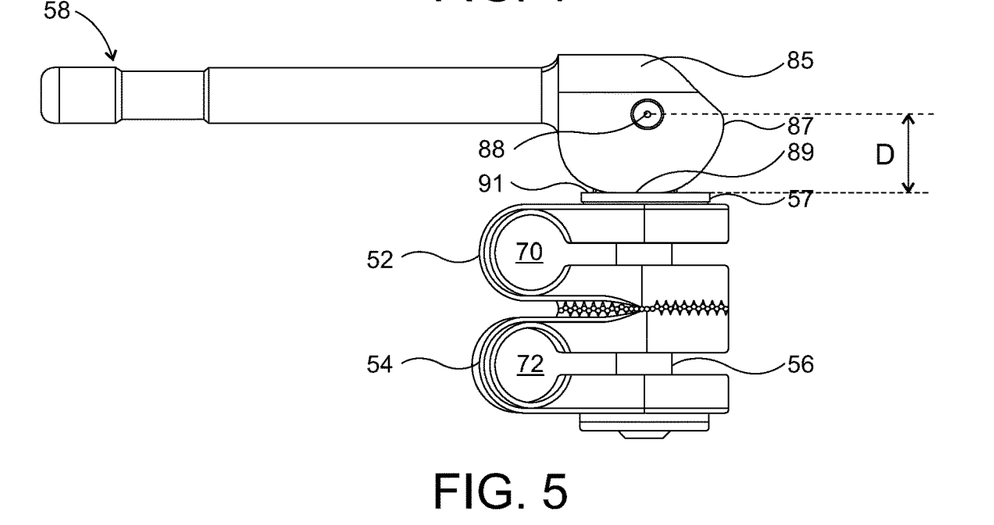
FIG. 5 is a side view of the universal clamping mechanism of FIG. 3 and in its closed position.
Figure 6:
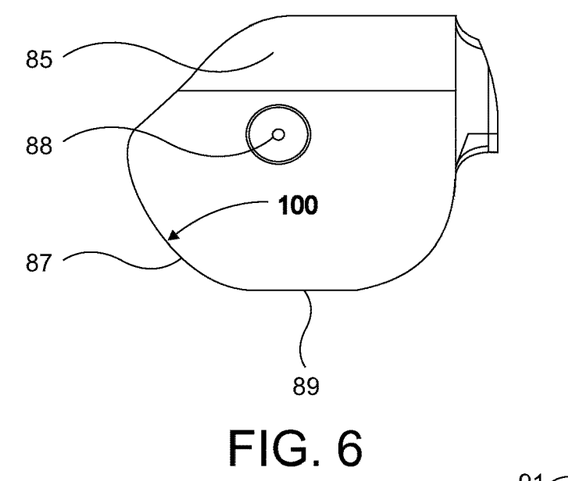
FIG. 6 is a side view of the cam head of the clamping mechanism of FIG. 3.

Referring now to FIG. 6, an outer edge 100 of the cam head 85 is eccentric, i.e. multiply curved, such that the distance D between the pivot axis 88 and the upper surface 91 of the washer 57 increases as the cam lever 58 is moved from its open position (e.g., FIG. 4) towards its closed position (e.g., FIG. 5). Hence, movement of cam lever 58 towards its closed position draws shaft 56 upwardly through cylindrical apertures 112, 116, compressing clamp members 52, 54 between the outer edge 100 of the cam head 85 and a stop, such as the nut 113, secured to the distal end of shaft 56. Compression of the resilient clamp members 52, 54 initially causes the sets locking teeth 99*a*, 99*b* to engage each other, thereby fixing the positions of the clamp members 52, 54 relative to each other. Further compression of clamp members 52, 54 constricts the area circumscribed by cylindrical passages 70, 72 to secure clamps 52, 54 to the arms passing through cylindrical passages 70, 72.

Rotation of cam lever 58 towards its open position moves shaft 56 downwardly through cylindrical apertures 112, 116. Due to the downward movement of shaft 56, the nut 113 may be urged away from aperture 116, thus reducing or removing a clamping force applied to resilient clamps 52, 53. At the open position, clamps 52, 54 are loosely held on shaft 56, and may be rotated relative to one another about shaft 56. The nut 113 may prevent clamps 52, 54 from being removed for the shaft 56. The removed or reduced compression on clamps 52, 54 may cause cylindrical passages 70, 72 to expand their diameter, allowing clamps 52, 54 to be moved relative to posts positioned in cylindrical passages 70, 72. The open position may also allow the various clamp components to be accessed for cleaning.

FIG. 4 shows the two clamps 52, 54 in their unclamped positions. Cam lever 58 is rotated upwardly to an open position for releasing or untightening of clamps 52, 54. In this open position, a release surface 87 of cam head 85 is moved or rotated to a position above washer 57 providing little or no contact between cam head 85 and washer 57 and reducing the distance D between the pivot axis 88 and the upper surface 91 of the washer 57. This removes the force on clamps 52, 54 allowing them to expand and open their respective passages 70, 72 to a full extent.

FIG. 5 shows the two clamps 52, 54 in their clamped positions. Cam lever 58 is rotated downwardly to a closed position for tightening of clamp 52, 54. In this closed position, release surface 87 is rotated away from washer 57 and a flat planar surface 89 of cam head 85 engages washer 57. To enter this closed position, a clamping force is applied to clamps 52, 54 which constricts passages 70, 72.

Planar surface 89 serves to lock handle 81 into position. Because surface 89 is a flat planar surface and contacts the flat planar top surface 91 of the washer 57, the reverse movement of cam lever 58 into an open position requires more force making it difficult for cam head 85 to unintentionally loosen and rotate away from its closed position of FIG. 5.

FIG. 6 is a side view of cam head 85 illustrating the surfaces 87, 89. Surfaces 87, 89 extend across the bottom of cam head 85. Surfaces 87, 89 are positioned on the cam head relative to axis 88 so as to engage the flat top surface 91 (FIG. 5) of washer 57 when the cam lever 58 is pivoted.

Referring to FIGS. 7A-7C and FIG. 8, washer 57 is generally cylindrical in shape, and has a cone-like configured shape at its bottom. Washer 57 includes an outer cylindrical surface 101 and a truncated cone surface 103. An aperture 105 extends fully through the washer terminating at the end of cone surface 103. Aperture 105 has a diameter to receive central shaft 56 (FIG. 4) which is cylindrical in shape.

Figure 10:
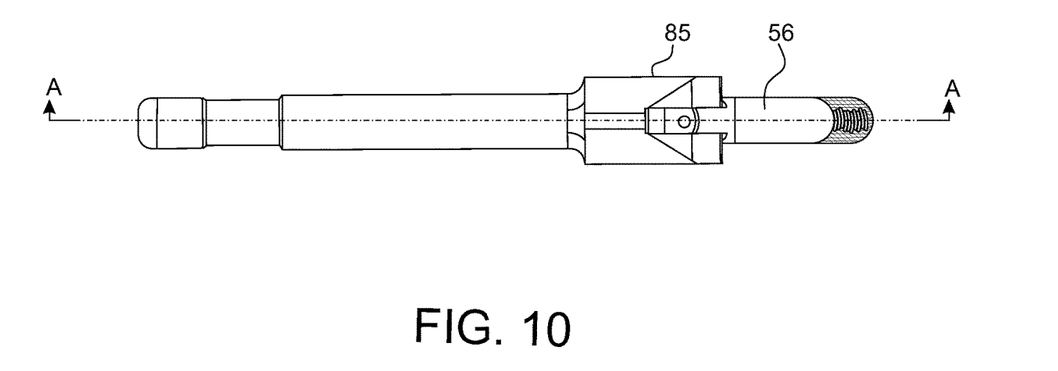
FIG. 10 is a top view of the clamping mechanism of FIG. 3.
Figure 11:
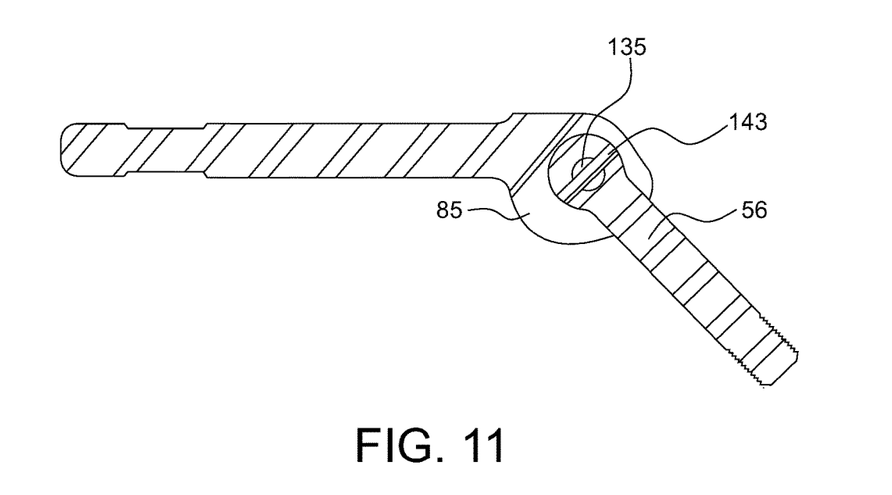
FIG. 11 is a cross sectional side view of the clamping mechanism of FIG. 9 along lines A-A.

Referring to FIGS. 4, 10 and 11, central shaft 56 extends into cam head 85 and is rotatably secured in place by a cam pivot pin 135. This allows pivoting of cam lever 58 into its open position (FIG. 4) and into its closed position (FIG. 5).

Figure 7A:
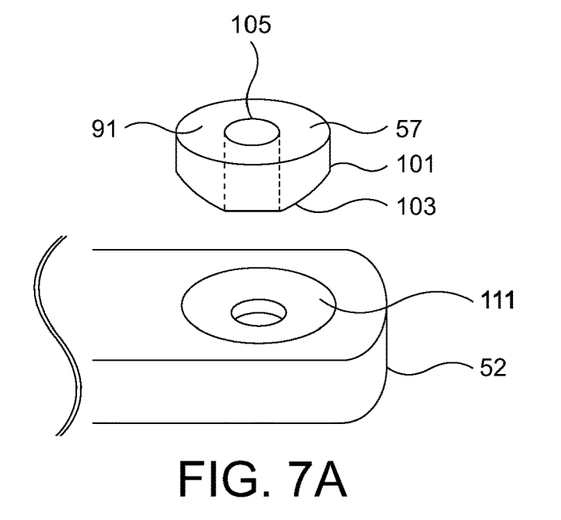
FIGS. 7A, 7B and 7C are views of a washer and a clamp of the clamping mechanism of FIG. 3.
Figure 7B:
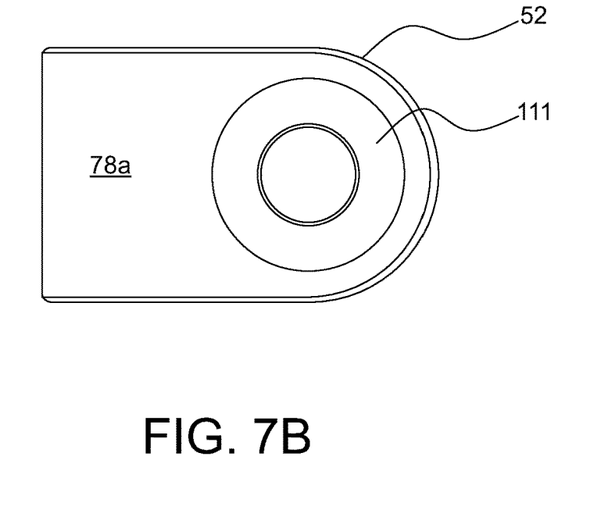
Figure 7C:
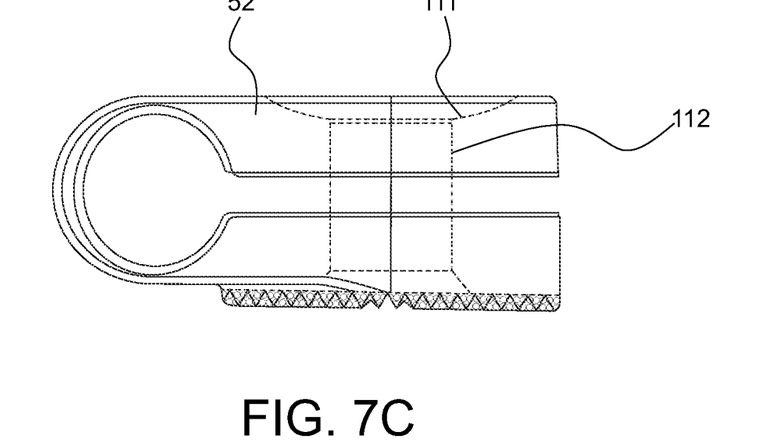
Figure 8:
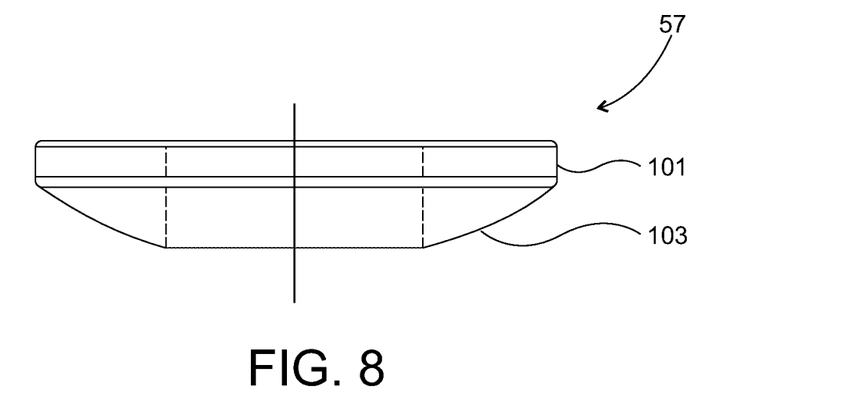
FIG. 8 is a side view of the washer of FIG. 7.
Figure 14:
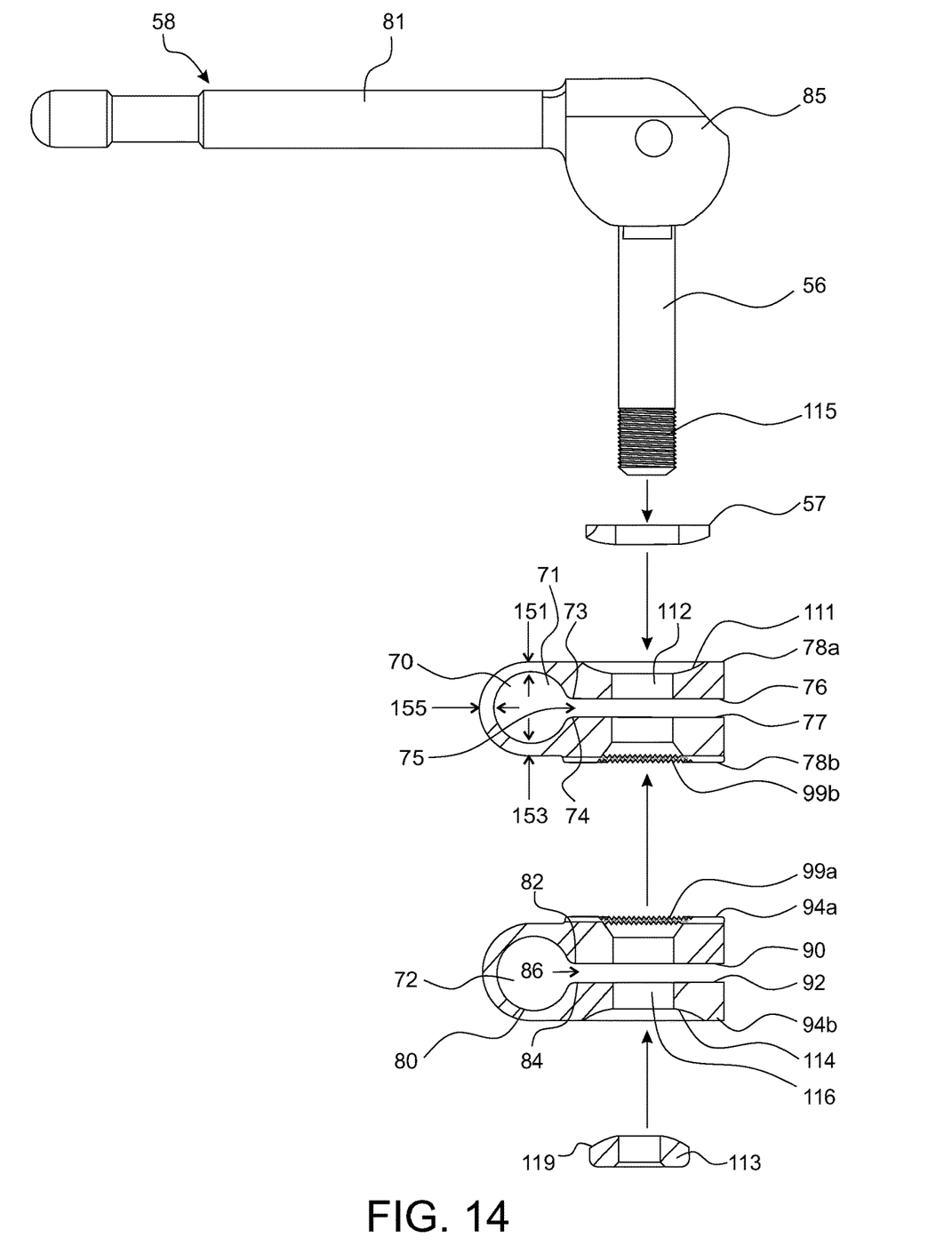
FIG. 14 is an exploded view of some components of the clamping mechanism of FIG. 3

Referring again to FIGS. 7A-7C, clamp 52 has a conically shaped aperture 111 to receive and mate with the conical surface 103 of washer 57. As shown in FIG. 7C, conical aperture 111 meets with cylindrical aperture 112 which has a diameter to receive central shaft 56. Similarly, clamp 54 has a conically shaped aperture 114 to receive and mate with the conical surface 119 of nut 113. See, FIG. 14. As shown in FIG. 14, conical aperture 114 meets with cylindrical aperture 116 which has a diameter to receive central shaft 56.

Figure 9:
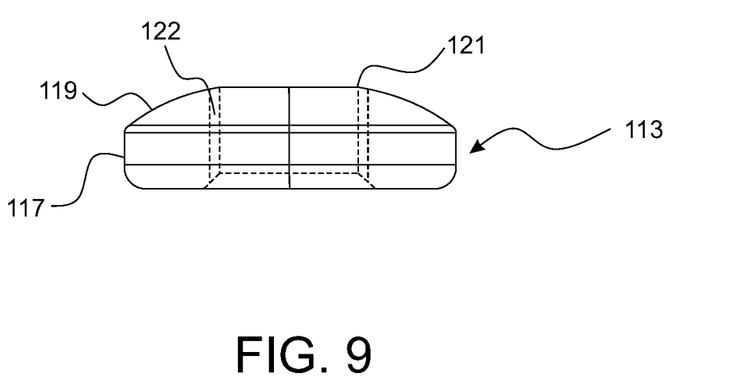
FIG. 9 is a side view of a washer of the clamping mechanism of FIG. 3.
Figure 12:
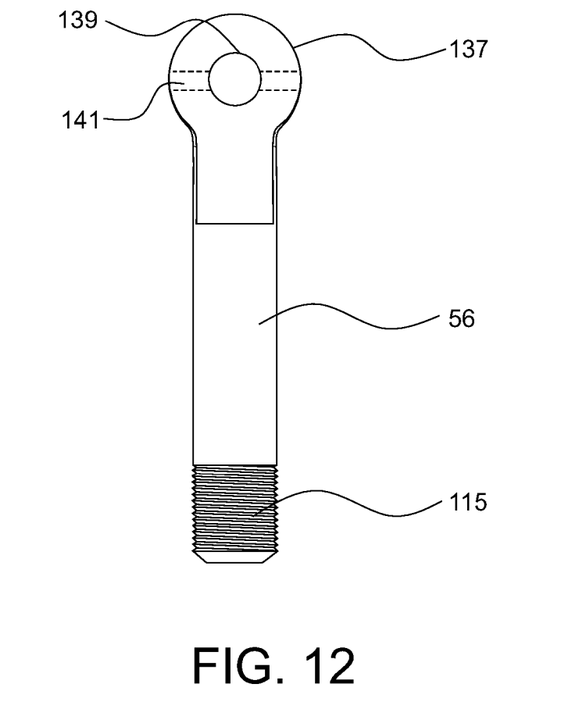
FIG. 12 is a side view of a shaft of clamping mechanism of FIG. 3.

As shown in FIG. 4, a nut 113 is threadedly secured onto the distal end of shaft 56. Threads 115 are shown in FIG. 12. Referring to FIG. 9, nut 113 is generally cylindrical in shape, having a cone-like configured shape at its top. Nut 113 includes a cylindrical surface 117 and a truncated cone surface 119. An aperture 121 extends fully through nut 113 terminating at the end of conical surface 119. Aperture 121 has a diameter to receive central shaft 56 and has threads 122 to mate with threads 115 on shaft 56 (FIG. 12).

The nut 113 may be welded to the shaft 56 after being threadedly secured to the distal end of the shaft 56. Such welding may prevent further rotation of the nut 113 in relation to the shaft 56 about a longitudinal axis of the shaft 56, but may permit rotation of the nut 113 with respect the clamps 52, 54 about the longitudinal axis of the shaft 56. Because nut 113 is rounded, the shaft 56 with welded nut 113 may be rotated 360°, even when nut 113 is partially drawn into aperture 116. This may permit the surgeon to rotate handle 81 to a convenient position, even after clamps 52, 54 have been compressed.

Prior to welding, the nut 113 may be rotated in one direction (e.g., clockwise) to tighten the nut 113 and increase a clamping force applied by the clamps 52, 54 and may be rotated in the opposite direction (e.g. counter-clockwise) to loosen the nut 113 and decrease the clamping force applied by the clamps 52, 54. In this manner, the clamping force of the clamps 52, 54 may be calibrated to a desired force. After obtaining the desired, calibrated clamping force, the nut 113 may be welded to ensure the nut 113 does not rotate further and the desired, clamping force is maintained.

Referring again to FIG. 3, cam head 85 is shaped to include two extending side members 123, 125 forming an interposed channel 127. Channel 127 is defined by two planar side surfaces 129, 131 (FIG. 13) of the side members 123, 125. Each side member includes a cylindrical aperture 133 (FIG. 3) which are aligned along their axis. A cam pin 135 (FIG. 3) passes through cylindrical apertures 133. Cam pin 135 is held fixed relative to cam head 85.

Figure 13:
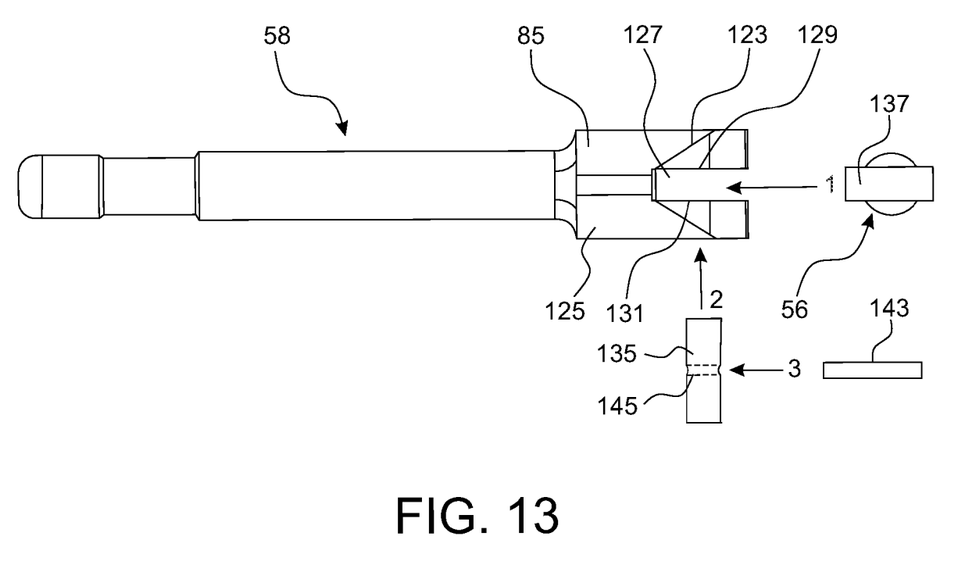
FIG. 13 is an exploded view of some components of the clamping mechanism of FIG. 3

As shown in FIG. 12, a top end 137 of the shaft 56 is generally planar in shape as best seen in FIG. 13, for movement within channel 127. Top end 137 (FIG. 12) includes a cylindrical aperture 139 for receiving cam pin 135 (FIG. 11) of cam head 85. Top end 137 rotates about cam pin 135. FIGS. 10 and 11 illustrate the shaft 56 being rotatably connected to cam pin 135.

As shown in FIG. 12, shaft 56 includes an additional cylindrical aperture 141 which passes through top end 137. Aperture 141 is located orthogonal to aperture 139, and aperture 141 is positioned to intersect with aperture 139, as shown in FIG. 12. Aperture 141 is sized to receive a lock pin 143, as shown in FIG. 11.

Referring to FIG. 13, the lever 58 is assembled, by initially positioning the top end 137 of shaft 56 into channel 127 of cam head 85. Cam pin 135 is next passed through apertures 133 (FIG. 3) in each of side members 123, 125 of the cam head and into aperture 139 (FIG. 12) of the shaft head. Finally, lock pin 143 (FIG. 13) is passed through aperture 141 (FIG. 12) located in the top end of shaft 56 and is passed through an aperture 145 in cam pin 135.

Thus, shaft 56 is held in position by both the aperture 139 in the shaft as well as the lock pin 143. Lock pin 143 secures the shaft 56 to the cam pin 135, and thus increases the wear surface between shaft 56 and the cam head 85.

Referring to FIG. 14, hole passages 70, 72 of the two clamps 52, 54 are shaped in an offset manner. Particularly, the wall thickness at 151 above each of hole passages 70, 72 and the wall thickness at 153 below each of hole passages 70, 72 is set at 0.070 inches. Whereas, the wall thickness at 155 between the hole and the distal end of the respective clamps is 0.100 inches. This, slight offset of the hole position serves to prevent the collapse of the hole due to continued use of the clamp without rods located in the hole passages 70, 72, e.g., without a retractor arm 44 (FIG. 1) or extension arms 19, 20 or cross bar 18 or post 17, within hole passages 70, 72.

Figure 15:
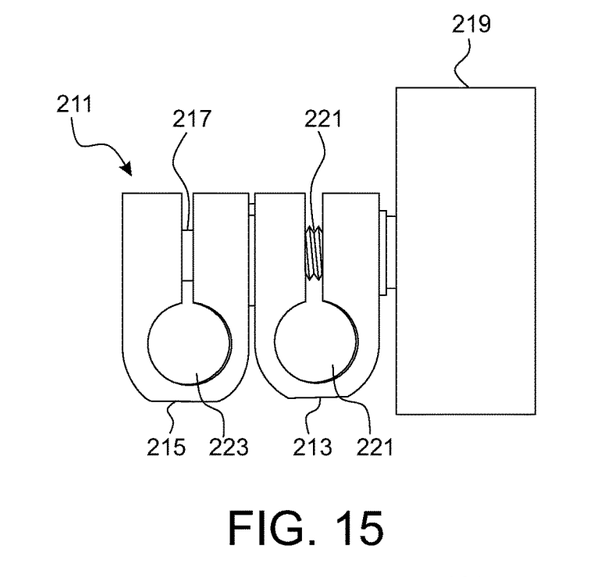
FIG. 15 is a side view of a second embodiment of a universal clamping mechanism.

As shown in FIG. 15, a second multi-directional joint clamp 211 includes a first clamp 213 and a second clamp 215. Joint clamp 211 includes a central shaft 217 as well as a turn-handle 219 for bringing first clamp 213 and second clamp 215 into a clamping position or into an unclamping position. Central shaft 217 includes a threaded portion 221 that mates with a second threaded portion (not shown) formed in the turn-handle 219. As the turn-handle 219 is rotated, shaft 217 is drawn upwardly into the turn-handle 219 moving the two clamps 213, 215 together in order to perform the clamping function.

First clamp 213 includes a passage 221 which is intended to accommodate, for example, post 17 of rail clamp 12 (FIG. 2). Similarly, second clamp 215 includes a passage 223. Passage 223 is intended to accommodate, for example, cross bar 18 (FIG. 2). Passages 221, 223 may be shaped in an offset manner similar to passages 70, 72 as described above in relation to FIG. 14.

Figure 16:
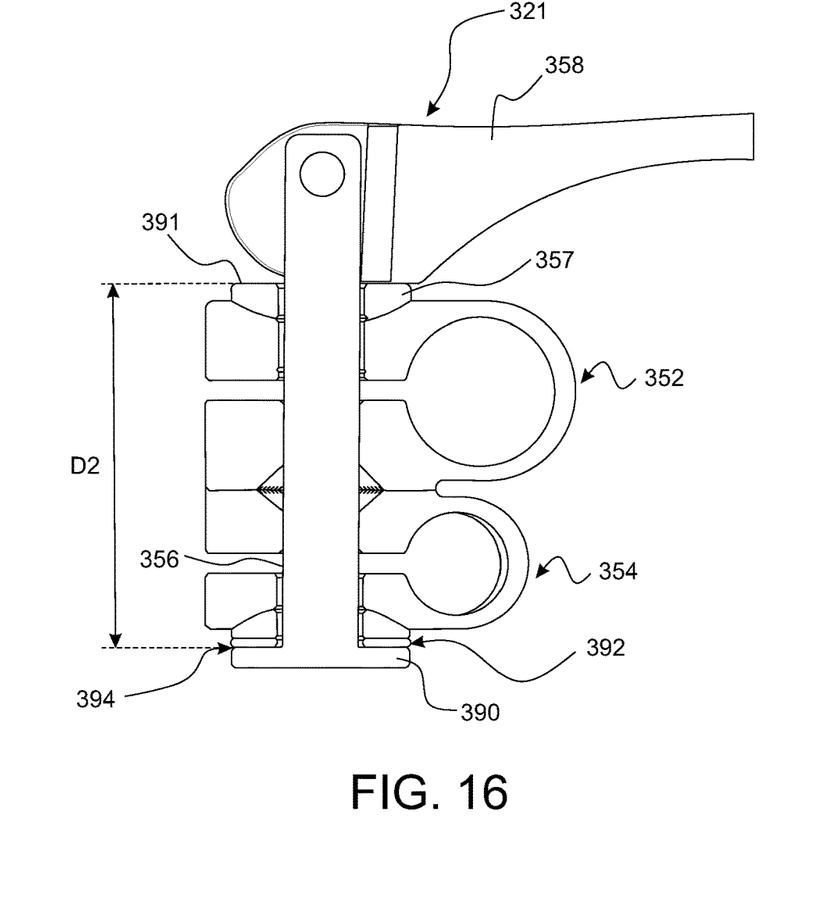
FIG. 16 is a side view of a third embodiment of a universal clamping mechanism.

Referring now to FIG. 16, a third multi-directional joint clamp 321 is shown. The third multi-directional joint clamp 321 may be implemented in a manner similar to the multi-directional joint clamp 21 of FIGS. 3-14. However, the joint clamp 321 of FIG. 16 uses a different type of stop for the central shaft. In particular, the joint clamp 321 may include a central shaft 356 with an integral or fixed head 390 at its distal end instead of a nut. The head 390 may engage a shim 392, which may adjust a distance D2 between a top surface 391 of the washer 357 and a top surface 394 of the integral head 390. A thicker shim 392 increases the distance D2 and thereby increases the pressure load placed on the clamps 352, 354 by the cam lever 358 when in a clamping position since the length of the shaft 356 remains unchanged. Conversely, a thinner shim 392 decreases the distance D2 and thereby decreases the pressure load placed on the clamps 352, 354. Thus, a desired pressure load may be obtained by selecting a shim 392 having an appropriate thickness. The multi-directional joint clamp 21 of FIGS. 3-14 may also adjust a pressure load applied by its cam lever 58. However, the multi-directional joint clamp 21 may achieve such result by tightening or loosening the nut 113 instead of or in addition to using a shim 392.

While particular embodiments of the invention have been shown, it will be understood that the invention is not limited thereto since modifications may be made by those skilled in the art, particularly in light of the foregoing teaching. It is, therefore, the appended claims which define the true spirit and scope of the invention.

What is claimed is:

1. A clamping apparatus comprising:
    an upper clamp comprising an upper clamp top side, an upper clamp bottom side, and a first passage having a first surface broken by two legs of the upper clamp that are separated by a first gap, wherein the upper clamp top side comprises a conical aperture;
    a lower clamp comprising a lower clamp top side, a lower clamp bottom side, and a second passage having a second surface broken by two legs of the lower clamp that are separated by a second gap;
    a washer comprising a top surface and a conical lower surface that mates with the conical aperture in the upper clamp top side;
    a shaft comprising a shaft upper portion and a shaft lower portion, wherein the shaft extends through the upper clamp, through the washer, and into the lower clamp via the lower clamp top side;
    a cam lever comprising a cam head pivotally attached to the shaft upper portion; and
    a lower device secured to the shaft lower portion via a coupling, wherein the coupling permits adjusting a clamping force between by the cam head and the lower device by permitting movement of the lower device along the shaft lower portion; and
    wherein the cam head comprises a cam head outer surface that causes the cam head to apply the clamping force between the cam head and the lower device when the cam lever is rotated to a clamping position.
2. The clamping apparatus of claim 1, wherein:
    the shaft lower portion comprises threads;
    the lower device comprises threads; and
    the coupling comprises the threads of the lower device engaged with the threads of the shaft lower portion.
3. The clamping apparatus of claim 1, wherein:
    the shaft lower portion comprises threads along an external surface;
    the lower device comprises internal threads; and
    the coupling comprises the internal threads of the lower device engaged with the threads along the external surface of the shaft lower portion.
4. The clamping apparatus of claim 1, wherein:
    rotation of the lower device in a first direction reduces a distance between the lower device and the cam head; and
    rotation of the lower device in a second direction opposite the first direction increases the distance between the lower device and the cam head.
5. The clamping apparatus of claim 1, wherein the lower device is welded to the lower shaft portion to retain the clamping force at a desired level.
6. The clamping apparatus of claim 1, wherein the cam head outer surface comprises a flat surface that applies the clamping force to the upper clamp top side when the cam lever is rotated to the clamping position.
7. The clamping apparatus of claim 6, wherein the flat surface of the cam head outer surface engages the washer and applies the clamping force to the upper clamp top side via the washer.
8. The clamping apparatus of claim 1, wherein the upper clamp is rotatable about an axis of the shaft relative to the lower clamp.
9. The clamping apparatus of claim 1, wherein the lower clamp bottom side comprises a conical aperture that mates with a conical upper surface of the lower device.
10. The clamping apparatus of claim 1, wherein the upper clamp bottom side comprises teeth that engage teeth of the lower clamp top side.
11. A clamping apparatus comprising:
    a shaft comprising a shaft first portion and a shaft second portion;
    a first clamp carried by the shaft, the first clamp comprising a first passage having a first surface broken by two legs of the first clamp that are separated by a first gap and a conical aperture in a second surface;
    a second clamp carried by the shaft, the second clamp comprising a second passage having a second surface broken by two legs of the second clamp that are separated by a second gap;
    a cam lever pivotally attached to the shaft first portion;
    a washer between the cam lever and the first clamp, wherein the washer comprises a first surface and a conical second surface opposite the first surface, and wherein the conical second surface mates with the conical aperture in the first clamp; and
    an adjustment device secured to the shaft second portion via a coupling, wherein the coupling permits adjusting a clamping force between by the cam lever and the adjustment device by permitting movement of the adjustment device along the shaft second portion; and
    wherein the cam lever applies the clamping force to the first clamp and the second clamp via the washer when the cam lever is rotated to a clamping position.
12. The clamping apparatus of claim 11, wherein:
    the shaft second portion comprises threads;
    the adjustment device comprises threads; and
    the coupling comprises the threads of the adjustment device engaged with the threads of the shaft second portion.
13. The clamping apparatus of claim 11, wherein:
    the shaft second portion comprises threads along an external surface;
    the adjustment device comprises internal threads; and
    the coupling comprises the internal threads of the adjustment device engaged with the threads along the external surface of the shaft second portion.
14. The clamping apparatus of claim 11, wherein:
    rotation of the adjustment device in a first direction reduces a distance between the adjustment device and the cam lever; and
    rotation of the adjustment device in a second direction opposite the first direction increases the distance between the adjustment device and the cam lever.
15. The clamping apparatus of claim 11, wherein the adjustment device is welded to the second shaft portion to retain the clamping force at a desired level.
16. The clamping apparatus of claim 11, wherein the cam lever comprises a flat surface that applies the clamping force to the first clamp when the cam lever is rotated to the clamping position.

17. The clamping apparatus of claim 16,
wherein the flat surface of the cam lever engages the washer and applies the clamping force to the first clamp via the washer.

18. The clamping apparatus of claim 11, wherein the first clamp is rotatable about an axis of the shaft relative to the second clamp.

19. The clamping apparatus of claim 11, wherein the second clamp comprises a conical aperture that mates with a conical upper surface of the adjustment device.

20. The clamping apparatus of claim 11, wherein the first clamp comprises teeth that engage teeth of the second clamp.

\* \* \* \* \*